United States Patent [19]

Ashley et al.

[11] 4,428,908
[45] Jan. 31, 1984

[54] RADIONUCLIDE QUALITY CONTROL TEST KIT

[76] Inventors: Sheldon J. Ashley; Meredith A. Ashley, both of 147-15 84th Rd., Jamaica, N.Y. 11435

[21] Appl. No.: 361,748

[22] Filed: Mar. 25, 1982

Related U.S. Application Data

[63] Continuation-in-part of Ser. No. 159,825, Jun. 16, 1980, abandoned.

[51] Int. Cl.³ ................. G01N 23/00; G01N 31/08
[52] U.S. Cl. ............................. 422/61; 210/658; 422/56; 436/1; 436/39; 436/57
[58] Field of Search ................. 422/56, 61; 210/658; 436/1, 39, 41, 57

[56] References Cited

U.S. PATENT DOCUMENTS

| | | | |
|---|---|---|---|
| 2,460,072 | 1/1949 | Davis | 436/41 |
| 3,046,779 | 7/1962 | Coleman | 210/658 X |
| 3,714,035 | 1/1973 | Jones | 210/658 X |
| 3,832,134 | 8/1974 | Sohn | 210/658 X |
| 4,094,647 | 6/1978 | Deutsch | 422/56 X |
| 4,095,950 | 6/1978 | Kahn | 210/658 X |
| 4,098,577 | 7/1978 | Halpern | 436/1 |
| 4,250,161 | 2/1981 | Schrijver | 422/61 X |
| 4,273,653 | 6/1981 | Uihlein | 210/658 X |

OTHER PUBLICATIONS

Chemical Abstracts, 88: 168031b (1978).
S. Archimandritis et al., Jour. of Radioanalytical Chemistry, vol. 43, 287–293 (1978).
"Aloe Scientif" catalog, p. 291, A. S. Aloe Co., St. Louis, 1952.

*Primary Examiner*—Sidney Marantz
*Attorney, Agent, or Firm*—Daniel Jay Tick

[57] ABSTRACT

A radionuclide quality control test kit includes a disposable chromatography chamber. A premeasured amount of a solvent solution is provided in the chamber. A disposable test strip has spaced opposite first and second ends. The first end is immersible in the solvent solution in the chamber upon being spotted by a radiopharmaceutical to be tested to enable the solvent solution to ascend the strip to the second end whereat radiochemical impurities of the radiopharmaceutical migrating to the second end are radiologically countable to permit computation of such impurities.

6 Claims, 9 Drawing Figures

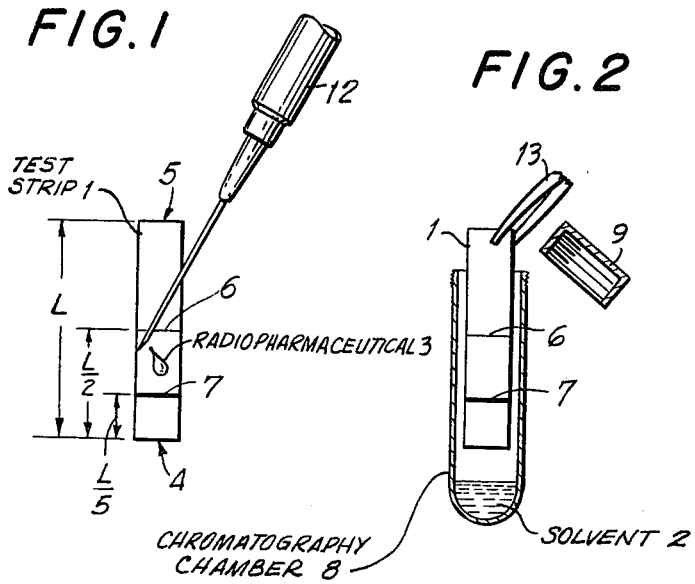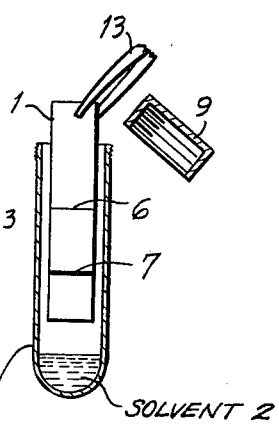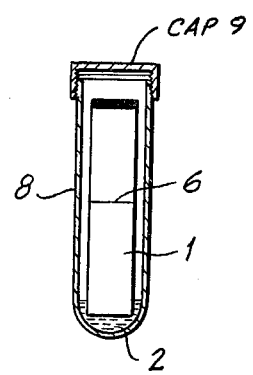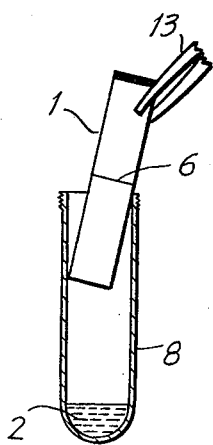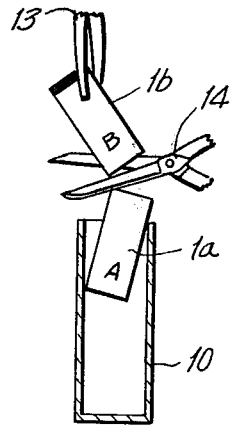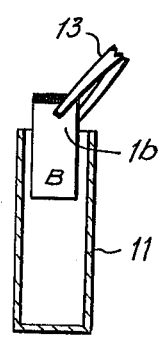

FIG. 7A

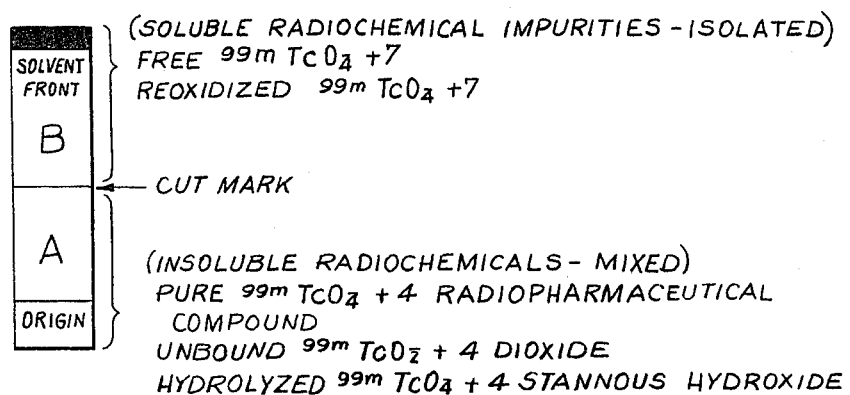

(SOLUBLE RADIOCHEMICAL IMPURITIES - ISOLATED)
FREE $^{99m}TcO_4^{+7}$
REOXIDIZED $^{99m}TcO_4^{+7}$

← CUT MARK (INSOLUBLE RADIOCHEMICALS - MIXED)
PURE $^{99m}TcO_4^{+4}$ RADIOPHARMACEUTICAL COMPOUND
UNBOUND $^{99m}TcO_2^{+4}$ DIOXIDE
HYDROLYZED $^{99m}TcO_4^{+4}$ STANNOUS HYDROXIDE

FIG. 7B

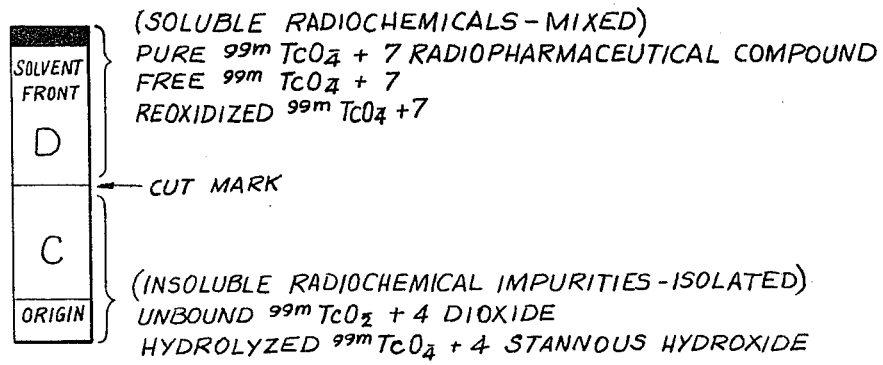

(SOLUBLE RADIOCHEMICALS - MIXED)
PURE $^{99m}TcO_4^{+7}$ RADIOPHARMACEUTICAL COMPOUND
FREE $^{99m}TcO_4^{+7}$
REOXIDIZED $^{99m}TcO_4^{+7}$

← CUT MARK (INSOLUBLE RADIOCHEMICAL IMPURITIES - ISOLATED)
UNBOUND $^{99m}TcO_2^{+4}$ DIOXIDE
HYDROLYZED $^{99m}TcO_4^{+4}$ STANNOUS HYDROXIDE

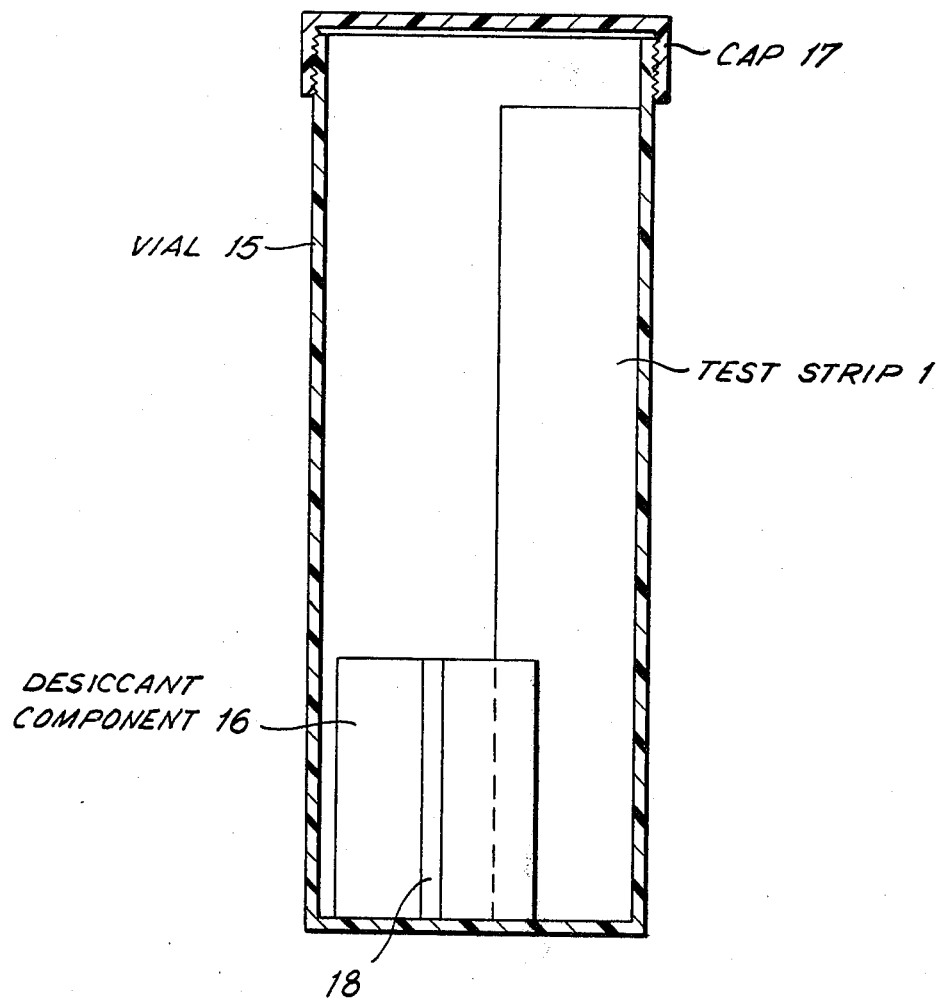

RADIONUCLIDE QUALITY CONTROL TEST KIT

BACKGROUND OF THE INVENTION

This is a continuation-in-part of application Ser. No. 159,825 for RADIONUCLIDE QUALITY CONTROL TEST KIT, filed June 16, 1980 and now abandoned.

The present invention relates to a radionuclide quality control test kit. More particularly, the invention relates to a radionuclide quality control test kit for determining the radiochemical purity of radiopharmaceutical compounds.

Technetium $Tc^{99m}$ tagged radiopharmaceutical compounds are used in nuclear medicine more frequently than any other available radionuclide. Research has isolated, identified, and thereby shown, radiochemical impurities to exist in some of these materials. Since the presence of impurities increases the radiation dose to non-target organs and organ systems and increases the probability of poor clinical images as well, there is invaluable benefit in instituting a program of quality control. The development of quality control tests such as, for example, instant thin layer chromatrography, which are sensitive to, and capable of, indicating the presence of radiochemical impurities, permits evaluation of materials prior to their use. The foundation for these tests resides in the understanding of $Tc^{99m}$ or $^{99m}Tc$ radiochemistry itself.

Technetium $Tc^{99m}$ pertechnetate is a man-made, water soluble, heavy metal. In order for it to be radiochemically pure, it must have a $+7$ chemical valence state, as does technetium in instant form and most generator eluate. However, technetium with a $+5$ valence state may, unfortunately, be eluted from a generator as well. Technetium $Tc^{99m}O_4^-+5$ is radiochemically impure, will not behave as predictably as radiochemically pure $Tc^{99m}O_4^-+7$, and will not participate properly in tagging certain pharmaceuticals such as, for example, Sn DTPA.

Although $Tc^{99m}O_4^-+7$ is radiochemically pure and relatively stable in air or water, it cannot tag cold kit preparations. The $Tc^{99m}O_4^-+7$ must be intentionally chemically reduced to $Tc^{99m}O_4^-+4$. It is this change, to a lower oxidation state, that makes the technetium available for chelation or tagging to other chemicals, proteins and particles, in order to form new radiopharmaceuticals.

Soluble stannous chloride Sn II, or tin, is the most popular reducing agent used today in commercial cold kits. Although Sn II is convenient and predictable, it has inherent drawbacks in that it reacts readily with water and oxygen, which are sources of impurity and cause hydrolyzation and oxidation, respectively. Such reactions can prevent the proper reduction of technetium, or cause the reducing agent to either inhibit or compete with the tagging of the radionuclide to the pharmaceutical. These reactions can be categorized so that the origin of the resulting impurities can be explained.

Stannous chloride can become oxidized to stannic chloride Sn IV. Once oxidized, it is no longer capable of reducing the technetium from the $+7$ to the $+4$ chemical valence state. The unreduced (free $Tc^{99m}O_4^-+7$ will not tag, and therefore becomes a radiochemical impurity in the compound. In an attempt to prevent this, cold kits are packed under nitrogen and manufacturers suggest avoiding the introduction of air into the reagent vial. The test kit of the invention utilizes a saturated solvent atmosphere in a chromatography chamber for the same reason, since, if this is not done, oxidation may occur on the strip during the test itself.

Stannous chloride can become hydrolyzed and cause the formation of stannous hydroxide, an insoluble tin colloid. This chemical impurity binds reduced technetium and forms a $Tc^{99m}$ stannous hydroxide complex. Then, as a radiocolloid impurity, it will have selective uptake in the reticuloendothelial system such as, for example, liver, spleen and bone marrow. It has been postulated that residual moisture which remains in a vial after freeze-drying may, in part, be responsible for causing hydrolysis. The test kit of the invention utilizes baked and dried test strips and stores such strips with a desiccant, in order to avoid this.

Technetium $Tc^{99m}O_4^-+4$ reduced with stannous chloride can become hydrolyzed and form $Tc^{99m}O_2+4$ technetium dioxide. This reduced-hydrolyzed form of technetium loses its water solubility before tagging the pharmaceutical. It remains unbound and subsequently becomes a radiochemical impurity in the compound. This may happen to a pure material sample on a moisture-saturated test strip.

Technetium $Tc^{99m}O_4^-+4$ which has already been bound to a pharmaceutical can reoxidize and revert back into $Tc^{99m}O_4^-+7$. Once again in its free form, the $Tc^{99m}O_4^-+7$ will not tag or remain tagged, thus creating a radiochemical impurity. The rate of reoxidation and the appearance of free technetium in the compound are prime factors which determine the expiration time of the material. The rate of reoxidation accelerates with an increase in the air content within the chromatography chamber or vial. This may happen to a pure test sample in a plain air-filled chromatography chamber without a saturated solvent atmosphere. It can be minimized by packing cold kits under nitrogen, and by avoiding the introduction of air into the reagent vial. Anti-oxidants such as, for example, ascorbic acid, may be used in an attempt to retard the rate or reoxidation too.

In terms of categorizing the impurities, it can be stated that insoluble radiochemical impurities are created by hydrolysis of the stannous chloride reducing agent and/or the technetium. Soluble radiochemical impurities are created by oxidation of the stannous chloride reducing agent and/or the technetium.

The commonly prepared $Tc^{99m}$ radiopharmaceutical compounds fall into the category of either insoluble radiopharmaceuticals such as, for example, Sn reduced proteins, or sulphur and thiol compounds, which are reduced by an agent other than tin, or soluble radiopharmaceuticals such as, for example, Sn chelate complexes.

A $Tc^{99m}$ compound cannot be radiochemically pure if it is made from impure technetium. Instant thin layer chromatography, utilizing the radionuclide quality control test kit of the invention, provides a means of determining $Tc^{99m}$ radiochemical impurities either prior to compounding the radiopharmaceutical, or in the tagged compound itself prior to injection. This may happen on the test strip. The principle of the test is relatively simple. When a radiopharmaceutical compound exists in its chemically pure form, it cannot be separated by ordinary chemical analysis. However, if the compound is not chemically pure, its pure and impure components can be separated.

The principal object of the present invention is to provide a radionuclide quality control test kit which eliminates the need for replenishment or reuse of solvents and does not permit the introduction of impurities in the test sample during analysis.

An object of the invention is to provide a radionuclide quality control test kit which eliminates the need for cleaning chromatography chambers.

Another object of the invention is to provide a radionuclide quality control test kit which avoids contamination in subsequent tests.

Still another object of the invention is to provide a radionuclide quality control test kit of simple structure, which is used with facility and convenience, and determines the radiochemical purity of radiopharmaceutical compounds with accuracy, efficiency and reliability.

Yet another object of the invention is to provide a radionuclide quality control kit which provides a saturated atmosphere in equilibrium with the vaporized solvent solution.

Another object of the invention is to provide a radionuclide quality control test kit having a test strip specially treated to remove moisture.

Still another object of the invention is to provide a radionuclide quality control test kit having test strips which are preserved to retain their sensitivity to detect and separate radiochemical impurities from the pure radionuclide.

Yet another object of the invention is to provide a radionuclide quality control test kit having a desiccant component providing a visual self-indication of the expiration time of the test strips and the test kit.

Another object of the invention is to provide a radionuclide quality control test kit having test strips which visually indicate the end point of the test, at which time the solvent solution has reached the uppermost end of the test strip.

Still another object of the invention is to provide a radionuclide quality control test kit which reduces test sample oxidation and introduction of impurities in the test sample.

Yet another object of the invention is to provide a radionuclide quality control test kit which reduces test sample hydration or hydrolyzation and introduction of impurities in the test sample.

Another object of the invention is to provide a radionuclide quality control test kit which uses a colored solvent solution as a solvent front indicator.

Still another object of the invention is to provide a radionuclide quality control test kit which includes a test strip having a first line which is used as a positive method for avoiding the mixture of a spotted sample too close to the solvent solution.

Yet another object of the invention is to provide a radionuclide quality control test kit which includes a test strip having a second line as a relative front indicator for use in measuring the separation of an impurity.

BRIEF SUMMARY OF THE INVENTION

In accordance with the invention, a radionuclide quality control test kit for determining the radiochemical purity of radiopharmaceutical compounds comprises a disposable chromatography chamber. A cap for closing the chromatography chamber to provide a saturated solvent atmosphere is removably affixed to the chamber. A premeasured amount of solvent solution is provided in the chamber. A disposable test strip has spaced opposite first and second ends. The first end is immersible in the solvent solution in the chamber upon being spotted by an insoluble radiopharmaceutical to be tested in a single solvent system to enable the solvent solution to ascend the strip to the second end whereat soluble radiochemical impurities of the radiopharmaceutical migrating to the second end are radiologically countable to permit computation of such impurities. The test strip has a length between the first and second ends. A first line is marked thereon in parallel relation with the first and second ends equidistantly from the ends. A second line is marked thereon in parallel relation with the first and second ends at approximately 1/5 the length of the strip from the first end. The strip is cuttable along the first line to divide it into two strips of equal length for testing impurities. A vial having a removable cap is provided for storing the strip. A color-indicating desiccant component is sealed in the vial with the strip.

An additional disposable chromatography chamber and an additional premeasured amount of an additional solvent solution in the additional chamber are provided. The first end of the test strip is immersible in the additional solvent solution in the additional chamber upon being spotted by a soluble radiopharmaceutical to be tested in a double solvent system to enable the additional solvent solution to ascend the strip to the second end. The soluble pure radiopharmaceutical migrates to the second end, leaving the insoluble radiochemical impurities at the first end and is radiologically countable to permit computation of such impurities.

The solvent solution consists of one, or a combination of, approximately 1.0 ml 85% methanol, methylethylketone, normal saline, acetone, acetonitrile, chloroform and water. Each solvent solution is dyed a different color, in accordance with a color code.

The solvent solution comprises a dye marker for visually indicating the ascent of the solvent solution and of the test end point when the solvent solution and dye reach the second end of the strip.

The color-indicating desiccant component comprises a color indicator area which visually indicates the expiration of the test kit and the test strip by changing the color of the area in accordance with the moisture of the vial storing the test strip.

The first line is provided at a predetermined relative front and determines separation distance of pure versus impure radiopharmaceutical compounds.

In accordance with the method of the invention of manufacturing a radionuclide quality control test kit, a spotting line is marked on a test strip for spotting a sample of a radiopharmaceutical compound at a predetermined distance from the level of a solvent in which the strip is immersed. The strip is baked at approximately 200° F. for approximately 30 minutes to dry out the strip and drive moisture from the test strip. The baked strip is sealed in a vial with a color-indicating desiccant component.

The method further comprises marking a first line on the test strip substantially equidistantly from its ends and in substantially parallel relation with the ends. The strip is cuttable along the first line. The spotting line is marked on the test strip in substantially parallel relation with the ends at approximately 1/5 the length of the strip from the first end.

BRIEF DESCRIPTION OF THE DRAWINGS

In order that the invention may be readily carried into effect, it will now be described with reference to the accompanying drawings, wherein:

FIG. 1 is a view of an embodiment of the disposable test strip of the radionuclide quality control test kit of the invention, illustrating the spotting thereof by a radiopharmaceutical to be tested;

FIG. 2 is a view of the embodiment of FIG. 1 and an embodiment of the disposable chromatography chamber of the radionuclide quality control test kit of the invention having a solvent solution therein, illustrating the placing of the strip in the solvent solution;

FIG. 3 is a view of the strip of FIGS. 1 and 2 immersed in the solvent solution of the capped chromatography chamber of FIG. 2;

FIG. 4 is a view of the strip of FIG. 3 being removed from the chromatography chamber of FIG. 3 after ascension of the solvent solution along the strip;

FIG. 5 is a view illustrating a step of the manual method of determining the radiochemical purity of the radiopharmaceutical spotted on the strip;

FIG. 6 is a view illustrating a following step of the manual method of determining the radiochemical purity of the radiopharmaceutical spotted on the strip;

FIG. 7A illustrates the radiochemical migration on developed test strips wherein there is isolation of soluble radiochemical impurities;

FIG. 7B illustrates the radiochemical migration on developed test strips wherein there is isolation of insoluble radiochemical impurities; and FIG. 8 is a view, on an enlarged scale, of the vial, storing the test strip and desiccant component of the radionuclide quality control test kit of the invention.

DETAILED DESCRIPTION OF THE INVENTION

The radionuclide quality control test kit of the invention contains the essential materials for determination of the radiochemical purity of technetium $Tc^{99m}$, technetium $Tc^{99m}$ tagged, sulphur colloid, macroaggregated albumin, human albumin microspheres, human serum albumin, DMSA, DTPA, phosphonates, phosphates, phytate, glucoheptonate, IDAS and PGS. Free $Tc^{99m}O_4^-+7$ and reoxidized $Tc^{99m}O_4^-+7$ are radiochemical impurities which may be separated from insoluble radiopharmaceutical compounds. Unbound $Tc^{99m}O_2+4$ dioxide and hydrolyzed $Tc^{99m}O_4^-+4$ stannous hydroxide, in addition to free $Tc^{99m}O_4^-+7$ and reoxidized $Tc^{99m}O_4^-+4$ are radiochemical impurities which may be separated from soluble radiopharmaceutical compounds. One method of accomplishing separation is by instant thin layer, silica gel or Whatman paper chromatography. Research and laboratory investigations conducted on test samples with known radiochemical impurities have shown that the test made with the test kit of the invention is sensitive to, and capable of indicating the presence of, such impurities. The test results should be used to determine whether or not the $Tc^{99m}$ radiopharmaceutical is suitable for clinical use. The test kit of the invention can measure radiochemical purity prior to the administration of the $Tc^{99m}$ radiopharmaceutical to the patient, thereby eliminating an increased radiation does to non-target organs and organ systems, while also reducing the probability of poor clinical images.

The chemical valence states of $Tc^{99m}$ are the keys to compounding radiopharmaceuticals. $Tc^{99m}O_4^-$, whether eluted from a generator prior to use or delivered as instant, should be in the $+7$ valence state. In the radiochemically pure $+7$ valence state, $Tc^{99m}$ cannot tag cold kits. The $Tc^{99m}+7$ must be chemically reduced to the $+4$ state in order for it to participate in the tagging process. The radiochemical purity of a radiopharmaceutical is related to the total reduction $Tc^{99m}+7 \rightarrow Tc^{99m}+4$ and the total bonding of $Tc^{99m}+4$ to the pharmaceutical carrier. The test kit of the invention detects radiochemical impurities which occur when a portion of the $Tc^{99m}$ remains unreduced, or still in the $+7$ state. $Tc^{99m}+7$ will not tag the carrier pharmaceutical and exists as free $Tc^{99m}$ in the radiopharmaceutical compound.

The test kit of the invention utilizes two opposing forces. A silica gel impregnated or Whatman paper test strip 1 retards the movement of one radiochemical substance. The test strip 1 thus functions as a stationary phase. The test strip 1 is prepared by initially heating it to 200° F. for a period of 30 minutes in order to drive all moisture out of the silica gel or Whatman paper strip.

A developing solvent 2 (FIGS. 2 to 4) functions as a mobile phase to provide a vehicle for the separation of other chemical substances. The solvent solution may comprise any suitable fluid such as, for example, approximately 1.0 ml 85% methanol, methylethylketone, normal saline, acetone, acetonitrile, chloroform or water, or any combination of these.

In order to perform the procedure, a drop of $Tc^{99m}$ tagged radiopharmaceutical 3 is spotted close to one end of the test strip 1, as shown in FIG. 1.

The test strip 1 (FIGS. 1 to 4) has a length L, which is preferably 8 to 10 cm, between spaced opposite first and second ends 4 and 5, respectively, as shown in FIG. 1. A first line 6 (FIGS. 1 to 4) is marked on the test strip 1 in parallel relation with the first and second ends, equidistantly from said ends. A second line 7 (FIGS. 1 and 2) is marked on the test strip 1 in parallel relation with the first and second ends at approximately 1/5 the length L of said strip from the first end 4, as shown in FIG. 1. The second line 7 is preferably 2 cm from the first end 4. The test strip is spotted at the second line 7, as shown in FIG. 1.

The second line 7 is a thin line marked on the test strip 1. After the line 7 has been made on the test strip 1, said strip is baked at 200° F. for 30 minutes. The test strip 1 is thereby immediately dried out and any moisture is driven from said strip. The baking is necessary to thoroughly dry out the strip, since if there is any moisture in said strip, the strip will be insensitive to separating the pure from the impure radiopharmaceutical and sample hydration or hydrolyzation may occur, causing impurities in the sample. This would make the mother batch falsely appear impure.

After the baking, the test strip 1 is immediately packed in a sealed container or vial 15 (FIG. 8) with approximately 1.0 gram color-indicating silica gel desiccant of any suitable type, which absorbs any moisture. A suitable desiccant component 16 (FIG. 8) is the MINI PAX which is a registered trademark of, and manufactured by, Multiform Desiccant Products, Inc., 1418 Niagara Street, Buffalo, N.Y. 14213. The vial 15 is sealed by a removable cap 17 (FIG. 8).

The first end 4 of the test strip 1, known as the origin of the strip, is placed in a chromatography chamber or vial 8 (FIGS. 2 to 4) which contains the color-coded, dyed developing solvent solution or solvent 2 in a premeasured amount. The colored solvent solution ascends the test strip 1 via absorption and capillary action until it reaches the second end 5 of said strip, known as the solvent front of said strip shown by dye (FIGS. 3 to 6). During this migration, various components of the compound separate and travel different distances in the direction of the solvent flow.

The soluble dye in the solvent solution 2 ascends the test strip 1, once said strip is placed in said developing solvent solution. This provides a visual indication of the test end point, at which time the solvent has ascended the test strip. This indication is the appearance of the dye at the second or uppermost end 5 of the test strip 1.

The expiration time of the test strip 1 is dependent upon its sensitivity, which, in turn, is dependent upon the dryness of said strip and the availability of the binding sites of the strip. When the test strip is treated and prepared in the aforedescribed manner, the desiccant component functions as a visual indicator of the expiration of the test kit and the test strip. This occurs when the test strip becomes saturated with moisture and the desiccant is no longer active. At such time, the desiccant component 16 color area changes color such as, for example, from blue to pink, thereby indicating expiration.

The test strip 1 is then removed from the developing or solvent solution 2, as shown in FIG. 4, and is either set aside to dry or is wet-wrapped in tape as a preparation for processing.

An internally threaded cap 9 (FIGS. 2 and 3) is removably affixed to the top of the chromatography chamber 8, which is externally threaded. The cap 9 closes the chromatography chamber 8, as shown in FIG. 3, to achieve a saturated atmosphere in equilibrium with the vaporized solvent solution. The cap 9 is lined with paper pulp and aluminum foil, a plastic insert, or other suitable material to prevent evaporation and loss of the solvent solution in the chromatography chamber 8.

The radionuclide quality control test kit of the invention permits the detection and measurement of radiochemical impurities in a radiopharmaceutical compound, as hereinbefore mentioned. The two types of radiochemical impurities in a radiopharmaceutical compound are hydrolysis, due to moisture and water, and oxidation, due to air or oxygen.

Applicants' novel test kit avoids the introduction of the two impurities or contaminants of hydrolysis and oxidation into the test procedure. No known test kit accomplishes this or removes these sources of impurity in its test preparations or methods. As a matter of fact, much of the time, in a normal test procedure, utilizing a known test kit, aside from the loss of sensitivity due to contaminants interfering with a test, in the testing of a pure radiopharmaceutical compound, the test procedure itself is the cause of the introduction of a contaminant of hydrolysis and/or oxidation into the test sample. The test sample is then analyzed as being impure and the whole batch of the material is labelled as having the impurities introduced by the test procedure whereas, as a matter of fact, the material is pure.

The baking of the test strips prior to packaging has a dual purpose. First, it dries the strip of moisture, which is a contaminant. Second, the silica gel, which is hygroscopic and therefore has an affinity for moisture, will block the separating properties of the test strip. Even if the hydrolysis were not a source of radiochemical impurity itself, the test would be insensitive to the detection of other varieties, either hydrolysis or oxidation, if the binding sites of the test strip are not available for separation.

The sealing of the desiccant component in the vial with the test strip is advantageous, since the introduction of inadvertent moisture is unavoidable due to the nature of the materials and the repeated opening and closing of the vial. The color indicator area 18 of the desiccant component 16 is thus of primary importance, since when the desiccant component is no longer active, the strips are saturated with moisture and the hydrolysis impurity will appear in the test sample even if it does not exist in the main batch of the readiopharmaceutical.

The solvent solution 2, which is premeasured to a proper extent in each chromatography chamber 8, is dyed with a different color for each test. The colored solvent solution 2 thus functions as a novel solvent front indicator and has the advantage of avoiding the introduction of moisture to the test strip from the soluble dye. The color indicator area 18 of the desiccant component 16 changes color such as, for example, blue to pink, when it changes from a dry condition to a moisture condition. Thus, when the color indicating area 18 changes its color, it indicates that there is moisture in the strip storage vial 15, the test strips 1 are saturated and the test kit is considered to have expired and is thus not to be used.

The first line 6 on the test strip 1 is functional, since it constitutes a specific point of measurement, introduced into the test procedure and indicates a reference point beyond which certain impurities should travel. This is known as a relative front or Rf. A relative front is an indication of the ratio or difference between the distance the solvent front, which is the colored solvent solution, travels along the test strip and the distance a specific radiochemical impurity travels along the same strip in the direction of the solvent flow. The relative front of a specific impurity is thus the signature of such impurity and each impure species is identifiable by its characteristic relative front.

The second line 7 is marked at a specifically calculated distance on the test strip, so that specific impurities are detected and differentiated from others. This is clearly understood when consideration is given the fact that the test strip is cut along the first line 6 for processing and the count of the radioactivity is based on how much of each portion of the strip is counted.

The first line 6 is the relative front, or Rf, point, beyond which impurities must separate in order to be detected. The second line 7 is a thin line and is far enough up the strip, so that the spotted sample will not mix with the solvent solution. The color-coded, dyed solvent solution visually indicates the ascent of the solvent solution and of the test end point when the solvent solution and dye reach the second end of the strip. It thus functions as a solvent front indicator.

The specific advantage of placing the solvent solution in the capped chromatography chamber 8 is also based on hydrolysis and oxidation in the test procedure. If there is an open vial or reservoir from which the chemicals are being dispensed, the resultant introduction of air and moisture is disadvantageous, as previously described. Many of the chemicals used such as, for example, acetone, are initially hygroscopic and will themselves be changed in property. Thus, the fact that the unit of solvent solution dispensed is a pure chemical quality, of spectrophotometric grade, because it is stored in a sealed tube, further insures its purity for the test. The sealing of the tube or chromatography chamber 8 is achieved by the cap 9. Even more important in this regard is the problem of introducing an impurity due to oxidation. The test sample may oxidize on the test strip, if the developing phase is carried out in an uncapped tube or in air. Furthermore, the binding sites on the test strip are of importance. These binding sites are saturated with the atmosphere of the solvent solution to permit proper separation of the components of the sample being tested. The binding sites of the test strip of the test kit of the invention are dry due to baking.

The proper amount of premeasured solvent solution in the tube precludes the possibility of too much solvent being dispensed into the chromatography chamber 8. If too much solvent were to be dispensed into the chromatography chamber 8, the spotted test sample would mix with the solvent solution and a false impurity would be introduced into the test sample results due to human error.

In actuality, the test kit of the invention includes a plurality of capped chromatography chambers and a plurality of test strips.

The testing of soluble radiopharmaceuticals requires that this procedure be repeated using a similar test strip and a separate different color-coded solvent.

A gamma radiation counting device of any suitable type such as, for example, a well scintillation counter, radiochromatogram scanner, or the like, is used to individually count the radioactivity in both the solvent front and the origin of the test strip, which may be separated by cutting the strip along the first line 6, at a known relative front, or Rf, as shown in FIG. 5. The chromatographic results are then obtained by combining these radiation readings in a mathematical formula representing the percentage of radiochemical impurity present in the sample.

In a manual method of utilizing the test kit of the invention with a well scintillation counter, or other suitable counter, two different counting chambers or vials 10 and 11 (FIGS. 5 and 6) are required to test insoluble radiopharmaceuticals. As shown in FIG. 5, the counting chamber 10 is used for counting the spotted origin 1a of the test strip 1, constituting the lower half of said test strip, where the radiochemical pure species resides; that is, bound, tagged radionuclide.

The solvent front 1b of the test strip 1, which is the upper half of said test strip, and which is where the radiochemical impurities such as, for example, free $Tc^{99m}$ have migrated, is placed in the counting chamber 11, as shown in FIG. 6.

Each of the counting chambers 10 and 11 is counted separately, for equal amounts of time, and the count rates are recorded. The appropriate background counts are then subtracted from the recorded count rate for each counting chamber and the test results are calculated by the formula hereinafter presented as Equation (1).

The specific mathematical formula necessary to these computations is dependent upon the type of $Tc^{99m}$ radiopharmaceutical being tested. Insoluble radiopharmaceuticals are processed once, in a single solvent system, providing one set of data, whereas soluble radiopharmaceuticals are processed twice, in a double solvent system, providing two sets of data.

The function of analyzing insoluble radiopharmaceuticals in a single solvent system such as, for example, 85% methanol, is to indicate the presence of any soluble radiochemical impurities in the compound such as, for example, free and/or reoxidized $Tc^{99m}$. These soluble impurities will separate from the rest of the radiopharmaceutical and migrate with the developing media toward the strip's solvent front. It should be noted that only soluble impurities such as, for example, free and/or reoxidized $Tc^{99m}$, is capable of separation and migration from insoluble radiopharmaceuticals. This creates a limitation in testing insoluble radiopharmaceuticals, since there is no way of separating any insoluble impurities such as, for example, unbound and/or hydrolyzed $Tc^{99m}$, from the insoluble pure radiopharmaceutical. Although detection of all types of impurities is not possible for insoluble radiopharmaceuticals, the importance of the procedure utilizing the test kit of the invention is that it does provide a means of ruling out one variety of impurities. Calculations are therefore derived by the formula $$\% \text{ free and/or reoxidized } Tc^{99m} = \frac{100 \times \text{``B'' counts}}{\text{``A''} + \text{``B'' counts}} \quad (1)$$

wherein the A counts are those of the spotted origin 1a (FIG. 5) and the B counts are those of the solvent front 1b (FIGS. 5 and 6).

As an example, it is assumed that chamber or vial 10 = 11,750 cpm and chamber or vial 11 = 135 cpm.

The upper half % impure =

$$\frac{100 \times B \text{ counts}}{A + B \text{ counts}} = \frac{100 \times 135}{11,750 + 135} = \frac{13,500}{11,885} = 1.14\%$$

The lower half % radiochemically pure =
$$100 - \% \text{ free} = 100 - 1.14 = 98.86\%$$

For purposes of quality control, an insoluble $Tc^{99m}$ radiopharmaceutical compound having $\geq 10\%$ free and/or reoxidized $Tc^{99m}$ is considered unacceptable for clinical use.

Double solvent systems provide a means of analyzing soluble radiopharmaceuticals, since their soluble nature permits separation of all types of impurities. The radiopharmaceutical is first tested for soluble impurities such as, for example, free and/or reoxidized $Tc^{99m}$, by using a solvent known to permit this separation such as, for example, methylethylketone, as described in the single solvent system. Insoluble impurities and the pure radiopharmaceutical remain at the origin (FIG. 7A). Therefore, the resulting computations via Equation 1 reflect only the % of free and/or reoxidized $Tc^{99m}$ in the compound. Analysis is performed using a second spotted test strip and a different solvent such as, for example, 0.9% saline, in order to isolate any insoluble impurities. The migration of soluble impurities and the pure radiopharmaceutical, which is made possible by this solvent, leaves only the insoluble impurities at the origin (FIG. 7B). Calculations for the second step of the double solvent system are derived by the formula $$\% \text{ unbound and/or hydrolyzed } Tc^{99m} = \frac{100 \times \text{``C'' counts}}{\text{``C''} + \text{``D'' counts}} \quad (2)$$

wherein the C counts are those of the spotted origin C (FIG. 7B) and the D counts are those of the solvent front D (FIG. 7B).

In order to determine the total radiochemical purity of a soluble $Tc^{99m}$ radiopharmaceutical, the results from both steps via Equations 1 and 2 of the double solvent system must be added together and subtracted from 100, as in the formula $$\% \text{ radiochemically pure } = \quad (3)$$

$$100 - \left|\begin{bmatrix} \% \text{ free and/or} \\ \text{reoxidized} \end{bmatrix} + \begin{bmatrix} \% \text{ unbound and/or} \\ \text{hydrolyzed} \end{bmatrix}\right|$$

For purposes of clinical use, the soluble $Tc^{99m}$ radiopharmaceutical compunds should have $\leq 10\%$ total combined radiochemical impurities and therefore be $\geq 90\%$ radiochemically pure.

The test strip 1 may be spotted by a hypodermic needle 12 (FIG. 1) and may be held by tweezers 13 (FIGS. 2, 4, 5 and 6). The strip 1 may be cut in half by a pair of scissors 14 at the aforedescribed relative front (FIG. 5).

While the invention has been described by means of a specific example and in a specific embodiment, we do not wish to be limited thereto, for obvious modifications will occur to those skilled in the art without departing from the spirit and scope of the invention.

We claim:

1. A radionuclide quality control test kit for determining the radiochemical purity of radiopharmaceutical compounds, said test kit comprising
  a disposable chromatography chamber;
  a cap for closing said chromatography chamber to provide a saturated solvent atmosphere, said cap being removably affixed to said chamber;
  a premeasured amount of solvent solution in the chamber, said solvent solution being dyed in accordance with a color code;
  a disposable test strip having spaced opposite first and second ends, said first end being immersible in the solvent solution in said chamber upon being spotted by an insoluble radiopharmaceutical to be tested in a single solvent system to enable said solvent solution to ascend said strip to said second end whereat soluble radiochemical impurities of the radipharmaceutical migrating to said second end are radiologically countable to permit computation of such impurities, said test strip having a length between said first and second ends, a first line marked thereon in parallel relation with said first and second end equidistantly from said ends and a second line marked thereon in parallel relation with said first and second ends at approximately 1/5 the length of said strip from said first end whereat said test strip is spottable at said second line and said strip is cuttable along said first line to divide it into two strips of equal length for testing for impurities;
  a vial having a removable cap for storing said strip; and
  a color-indicating desiccant component sealed in said vial with said strip.

2. A radionuclide quality control test kit as claimed in claim 1, further comprising an additional disposable chromatography chamber and an additional premeasured amount of an additional solvent solution in the additional chamber, and wherein said first end of said test strip is immersible in the additional solvent solution in the additional chamber upon being spotted by a soluble radiopharmaceutical to be tested in a double solvent system to enable said additional solvent solution to ascend said strip to said second end, the soluble pure radiopharmaceutical migrating to said second end leaving the insoluble radiochemical impurities at said first end and being radiologically countable to permit computation of such impurities.

3. A radionuclide quality control test kit as claimed in claim 1, wherein said solvent solution consists of one or a combination of approximately 1.0 ml 85% methanol, methylethylketone, normal saline, acetone, acetonitrile, chloroform and water.

4. A radionuclide quality control test kit as claimed in claim 1, wherein said solvent solution comprises a dye marker for visually indicating the ascent of the solvent solution and of the test end point when said solvent solution and dye reach the second end of said strip, thereby functioning as a solvent front indicator.

5. A radionuclide quality control test kit as claimed in claim 1, wherein said desiccant component comprises a color indicator area for visually indicating the expiration of said test kit and said test strip by changing the color of said area in accordance with the moisture of the vial storing the test strip.

6. A radionuclide quality control test kit as claimed in claim 1, wherein said first line is provided at a predetermined relative front and determines separation distance of pure versus impure radiopharmaceutical compounds.

* * * * *